United States Patent
Baldassarre et al.

(10) Patent No.: US 12,227,467 B2
(45) Date of Patent: Feb. 18, 2025

(54) PROCESS FOR BIO-1,3-BUTANEDIOL PURIFICATION FROM A FERMENTATION BROTH

(71) Applicant: VERSALIS S.P.A., San Donato Milanese (IT)

(72) Inventors: Mario Baldassarre, Novara (IT); Alberto Cesana, Novara (IT); Fabrizio Bordes, Novara (IT)

(73) Assignee: Versalis S.P.A., San Donato Milanese (IT)

(*) Notice: Subject to any disclaimer, the term of this patent is extended or adjusted under 35 U.S.C. 154(b) by 873 days.

(21) Appl. No.: 17/277,968

(22) PCT Filed: Sep. 19, 2019

(86) PCT No.: PCT/EP2019/075123
§ 371 (c)(1),
(2) Date: Mar. 19, 2021

(87) PCT Pub. No.: WO2020/058381
PCT Pub. Date: Mar. 26, 2020

(65) Prior Publication Data
US 2021/0380512 A1    Dec. 9, 2021

(30) Foreign Application Priority Data
Sep. 21, 2018 (IT) .......... 102018000008820

(51) Int. Cl.
*C07C 29/76* (2006.01)
*B01D 15/36* (2006.01)
(Continued)

(52) U.S. Cl.
CPC ............ *C07C 29/76* (2013.01); *B01D 15/362* (2013.01); *B01D 15/363* (2013.01);
(Continued)

(58) Field of Classification Search
None
See application file for complete search history.

(56) References Cited

U.S. PATENT DOCUMENTS

| 2005/0069997 A1 | 3/2005 | Adkesson et al. |
| 2011/0003355 A1* | 1/2011 | Clark ............... C07C 29/76 |
| | | 435/158 |

(Continued)

FOREIGN PATENT DOCUMENTS

| CN | 103890185 A | 6/2014 |
| CN | 105209414 A | 12/2015 |

(Continued)

OTHER PUBLICATIONS

Chinese First Office Action dated Jan. 5, 2023 from corresponding Chinese Patent Application No. 201980076779.6, 16 pages.
(Continued)

*Primary Examiner* — Medhanit W Bahta
(74) *Attorney, Agent, or Firm* — Ruggiero McAllister & McMahon LLC

(57) ABSTRACT

A process for bio-1,3-butanediol purification from a fermentation broth includes the steps of: (a) subjecting the fermentation broth to separation, (b) subjecting the product obtained in step (a) to treatment with ion-exchange resins, (c) subjecting the product obtained in step (b) to a first evaporation, (d) subjecting the product obtained in step (c) to a second evaporation; and (e) subjecting the product obtained in step (d) to a third evaporation, obtaining purified bio-1,3-butanediol. The purified bio-1,3-butanediol can be used to produce bio-1,3-butadiene. Bio-1,3-butadiene can be used as a monomer or as an intermediate to produce elastomers and (co)polymers.

17 Claims, 2 Drawing Sheets

(51) Int. Cl.
  B01D 21/26 (2006.01)
  B01D 61/02 (2006.01)
  B01D 61/14 (2006.01)
  B01D 61/58 (2006.01)
  B01D 69/02 (2006.01)
  B01J 23/10 (2006.01)
  C07C 1/24 (2006.01)
  C07C 29/80 (2006.01)
  C07C 31/20 (2006.01)
  C08F 36/06 (2006.01)
  C12P 7/18 (2006.01)

(52) U.S. Cl.
  CPC ......... B01D 21/262 (2013.01); B01D 61/027 (2013.01); B01D 61/147 (2013.01); B01D 61/58 (2013.01); B01D 69/02 (2013.01); B01J 23/10 (2013.01); C07C 1/24 (2013.01); C07C 29/80 (2013.01); C08F 36/06 (2013.01); C12P 7/18 (2013.01); *B01D 2325/02834* (2022.08); *B01D 2325/34* (2013.01)

(56) References Cited

U.S. PATENT DOCUMENTS

2014/0275465 A1    9/2014   Garikipati et al.
2017/0313633 A1*  11/2017   Vecchini ................ C07C 29/60

FOREIGN PATENT DOCUMENTS

| CN | 105793429 A | 7/2016 |
| CN | 107074677 A | 8/2017 |
| EP | 2767589 A1 | 8/2014 |
| JP | 61-65834 S | 4/1986 |
| JP | 2007-502325 A | 2/2007 |
| JP | 2012-528885 A | 11/2012 |
| JP | 2016-516096 A | 6/2016 |
| JP | 2017031170 A | 2/2017 |
| JP | 2017-537876 A | 12/2017 |
| WO | 2014/170759 A2 | 10/2014 |
| WO | 2013/054874 A1 | 3/2015 |
| WO | 2016092063 A1 | 6/2016 |
| WO | 2018/073282 A1 | 4/2018 |
| WO | WO-2018183628 A1 * 10/2018 ........... B01D 15/361 |

OTHER PUBLICATIONS

Japanese Notice of Reasons for Refusal dated Jun. 21, 2023 from corresponding Japanese Patent Application No. 2021-515445, 6 pages.

International Search Report dated Nov. 27, 2019 for PCT application No. PCT/EP2019/075123.

Written Opinion dated Nov. 27, 2019 for PCT application No. PCT/EP2019/075123.

* cited by examiner

PROCESS FOR BIO-1,3-BUTANEDIOL PURIFICATION FROM A FERMENTATION BROTH

CROSS-REFERENCE TO RELATED APPLICATIONS

This application is a national stage application, filed under 35 U.S.C. § 371, of International Patent Application No. PCT/EP2019/075123, filed on Sep. 19, 2019, which claims priority to Italian Patent Application 102018000008820, filed on Sep. 21, 2018, the entire contents of each of which is incorporated by reference herein in its entirety.

BACKGROUND OF THE DISCLOSURE

1. Field of the Disclosure

The present invention relates to a process for bio-1,3-butanediol purification from a fermentation broth.

More particularly, the present invention relates to a process for purification of bio-1,3-butanediol from a fermentation broth comprising the following steps: (a) subjecting the fermentation broth to separation; (b) subjecting the product obtained in step (a) to treatment with ion-exchange resins; (c) subjecting the product obtained in step (b) to a first evaporation; (d) subjecting the product obtained in step (c) to a second evaporation; (e) subjecting the product obtained in step (d) to a third evaporation, obtaining purified bio-1,3-butanediol.

Said purified bio-1,3-butanediol may advantageously be used for the production of bio-1,3-butadiene, which in turn may advantageously be used as a monomer or as an intermediate in the production of elastomers and (co)polymers.

Therefore, a further subject matter of the present invention is a process for the production of bio-1,3-butadiene from purified bio-1,3-butanediol obtained as described above, as well as the use of said bio-1,3-butadiene as a monomer or as an intermediate in the production of elastomers and (co)polymers.

It should further be noted that from said process for the production of bio-1,3-butadiene, in particular from the dehydration of bio-1,3-butandediol, other alkenols are obtained, namely bio-2-buten-1-ol (crotyl alcohol), bio-3-buten-2-ol (methylvinylcarbinol), bio-3-buten-1-ol (allylcarbinol), more particularly bio-2-buten-1-ol (crotyl alcohol) and bio-3-buten-2-ol (methylvinylcarbinol), which may advantageously be used, aside from in the production of bio-1,3-butadiene, in the production of intermediate which may in turn be used in fine chemistry, in agricultural chemistry, in pharmaceutical chemistry or in petrochemistry.

For the purpose of the present description and of the following claims, the term bio-2-buten-1-ol (crotyl alcohol) refers to: the mixture of cis and trans isomers, to the cis isomer alone, and to the trans isomer alone.

For example, bio-2-buten-1-ol (crotyl alcohol) may be used as a precursor to halides, crotyl esters, or crotyl ethers which may in turn be used, for example, as intermediates in the production of monomers, in fine chemistry (for example, for the production of sorbic acid, trimethylhydroquinone, crotonic acid, 3-methoxybutanol), in agricultural chemistry, in pharmaceutical chemistry.

2. Description of Related Art

Bio-3-buten-2-ol (methylvinylcarbinol) may be used as a solvent, in fine chemistry, as a component in the modification of polymers such as, for example, polyolefins (as described, for example, in German patent DE 1,908,620).

Bio-3-buten-1-ol (allylcarbinol) may be used, for example, as a raw material in pharmaceutical chemistry, in agricultural chemistry, in perfumes, in resins. For example, from the coupling reaction of bio-3-buten-1-ol (allylcarbinol) with aryl halides, catalysed by palladium, aryl-substituted aldehydes are obtained which may be used in pharmaceutical chemistry, for example, as antifolics.

Processes for the purification of polyols are known in the art.

For example, American patent U.S. Pat. No. 6,361,983 relates to a process for isolating one or more polyols, in particular 1,3-propanediol (1,3-PDO), from a fermentation broth, comprising the following steps: (a) adding a base to the fermentation broth to increase the pH above 7; and (b) isolating the polyol, in particular 1,3-propanediol, from the fermentation broth. Polyols of particular interest are 1,3-propanediol, 1,4-butanediol, glycerol, ethylene glycerol. The isolation step (b) is carried out by evaporation, distillation, filtration, extraction or crystallisation. Said process may further comprise a step (c) of removing precipitated solids which are present in the product obtained from step (b), by 1) filtration or centrifugation or 2) distillation under vacuum. In said patent, 1,3-butanediol is not specifically cited.

American patent U.S. Pat. No. 7,919,658 relates to a process for purification of bio-1,3-propanediol from a fermentation broth obtained from a microorganism capable of producing 1,3-propanediol, comprising the following steps in order: (a) subjecting the fermentation broth to filtration; (b) subjecting the product obtained in step (a) to two steps of purification by ion exchange comprising: (i) anion exchange and (ii) cation exchange to remove the ionic impurities; (c) subjecting the product obtained in step (ii) to chemical reduction; and (d) subjecting the product obtained in step (c) to at least two distillation processes comprising at least two distillation columns, wherein one of said distillation columns removes the molecules having a boiling point higher than the boiling point of the 1,3-propanediol and the other removes the molecules having a boiling point lower than the boiling point of the 1,3-propanediol; obtaining a purified bio-1,3-propanediol having a total concentration of impurities lower than about 400 ppm, an absorbance at 275 nm lower than 0.075, and a b* colour value (CIE L*a*b*) lower than about 0.15.

International patent application WO 2014/141780 relates to a process for isolating 1,4-butanediol (1,4-BDO) from a fermentation broth, comprising separating a liquid fraction enriched in 1,4-BDO from a solid fraction comprising cells, removing the water from said liquid fraction, removing the salts from said liquid fraction, and purifying 1,4-BDO. Said process comprises various steps such as: cells: removal (centrifugation and/or microfiltration and/or ultrafiltration), water and light compounds removal by means of an evaporation system comprising a double- or triple-effect evaporator, salts: removal by means of nanofiltration and/or ion-exchange resins and/or precipitation and/or crystallisation. Said patent application states that the process described therein may easily be modified for the purpose of isolating 1,3-butanediol: however, no examples to this effect are given.

American patent application US 2014/0275465 relates to a process for purification of 1,4-butanediol (1,4-BDO) comprising: (a) subjecting a raw mixture of 1,4-BDO to a first distillation column to remove the compounds having a boiling point lower than that of 1,4-BDO, obtaining a first stream containing 1,4-BDO; and (b) subjecting said first stream containing 1,4-BDO to a second distillation column to remove the compounds having a boiling point higher than that of 1,4-BDO, obtaining a first stream of high-boiling compounds, so as to produce purified 1,4-BDO, said purified 1,4-BDO being extracted laterally from said second column. 1,3-butanediol is cited among the compounds which may be purified using said process: however, no examples to this effect are given.

American patent U.S. Pat. No. 9,533,931 relates to a process for the production of 1,4-butanediol comprising the following steps: (a) adding an alkaline substance other than ammonia compounds and other than amine compounds to an aqueous solution containing 1,4-butanediol originating from a fermentation broth; (b) distilling the mixture obtained in step (a); and (c) recovering a solution containing 1,4-butanediol from a vapour flow; wherein, before said alkaline substance is added, said aqueous solution containing 1,4-butanediol originating from a fermentation broth is subjected to a nanofiltration step from which the permeate is recovered; and/or to an ion-exchange step. The purified 1,4-butanediol obtained is said to be advantageously used as a material for the production of polyester.

However, said processes of isolating and purifying 1,3-propanediol or 1,4-butanediol from the fermentation broth may present some difficulties. For example, said processes require steps of purification through the use of one or more distillation columns with a resulting lengthening of the process times and increase in the process costs.

Further, even though some of said processes are said also to be applicable to the purification of 1,3-butanediol, one of the critical steps of purifying 1,3-butanediol is the distillation. Indeed, the presence in the fermentation broth of specific contaminants [for example, 4-hydroxy-2-butanone (4-OH-2B)] which differ, even if only in concentration, from those present in the fermentation broths for producing other diols may bring about uncontrolled reactions during the distillation itself.

Indeed, it is known, as described for example by Ichikawa N. et al. in "Catalysis Communications" (2005), Vol. 6, pp. 19-22, that 4-hydroxy-2-butanone (4-OH-2B) may dehydrate to 3-buten-2-one (MVK) even at low temperatures (for example, 100° C.-120° C.), promoted by the presence of acid sites. The presence of a ketone during the distillation of the solution containing 1,3-butanediol may lead to the formation of a ketal by reaction between 1,3-butanediol and 3-buten-2-one (MVK), which pollutes the fractions containing purified 1,3-butanediol which, even if successfully removed, leads to the loss of a portion of 1,3-butanediol and thus to reduction in the yield of the process [as may be seen from Example 3 (comparative) below reported]. If said solution containing 1,3-butanediol is distilled under high vacuum, the formation of the 3-buten-2-one (MVK) and thus the formation of ketal is inhibited, but, for the same column used, this brings about an increase in the dwell times of said solution in the boiler, with a resulting increase in the thermal decomposition products of the 1,3-butanediol. [As may be seen from Example 4 (comparative) below reported]

The Applicant has therefore set itself the problem of finding a process for the purification of bio-1,3-butanediol from a fermentation broth which is capable of overcoming the drawbacks above reported.

SUMMARY OF THE DISCLOSURE

The Applicant has now found that by avoiding the distillation steps known in the art, and by using a first, a second and a third evaporation step, the drawbacks discussed above may be overcome. In particular, the Applicant has found a process for the purification of bio-1,3-butanediol from a fermentation broth comprising the following steps: (a) subjecting the fermentation broth to separation; (b) subjecting the product obtained in step (a) to treatment with ion-exchange resins; (c) subjecting the product obtained in step (b) to a first evaporation; (d) subjecting the product obtained in step (c) to a second evaporation; (e) subjecting the product obtained in step (d) to a third evaporation, obtaining purified bio-1,3-butanediol.

Many advantages are achieved by way of the aforementioned process. For example, said process makes it possible to avoid both the formation of the ketal by reaction between bio-1,3-butanediol and bio-3-buten-2-one (MVK) and the thermal decomposition of the bio-1,3-butanediol, with a resulting increase in the process yield. Further, by avoiding the use of distillation columns, both the system and the process are simplified, with a resulting saving both in economic terms and in terms of process times.

Further, said process makes it possible to obtain a purified bio-1,3-butanediol which may advantageously be used for the production of bio-1,3-butadiene which, in turn, may advantageously be used as a monomer or as an intermediate in the production of elastomers and (co)polymers.

Therefore, a further subject matter of the present invention is a process for the production of bio-1,3-butadiene from purified bio-1,3-butanediol obtained as described above, as well as the use of said bio-1,3-butadiene as a monomer or as an intermediate in the production of elastomers and (co)polymers.

The subject matter of the present invention therefore includes a process for bio-1,3-butanediol purification from a fermentation broth comprising the following steps:
(a) subjecting the fermentation broth to separation;
(b) subjecting the product obtained in step (a) to treatment with ion-exchange resins;
(c) subjecting the product obtained in step (b) to a first evaporation;
(d) subjecting the product obtained in step (c) to a second evaporation;
(e) subjecting the product obtained in step (d) to a third evaporation, obtaining purified bio-1,3-butanediol.

For the purpose of the present description and of the following claims, the definitions of numerical ranges always include the endpoints unless stated otherwise.

For the purpose of the present description and of the following claims, the term "comprising" also includes the terms "substantially consisting of" or "consisting of".

For the purpose of the present description and of the following claims, the term "purified bio-1,3-butanediol" indicates that at the end of the process according to the present invention, i.e. at the end of the third evaporation step (e), an aqueous solution is obtained in which:
  bio-1,3-butanediol is present at a concentration higher than or equal to 85% by weight, preferably higher than or equal to 90% by weight, based on the total weight of said aqueous solution;
  water is present at a concentration lower than or equal to 15% by weight, preferably lower than or equal to 8% by weight, based on the total weight of said aqueous solution;
  any organic impurities [for example, acids, 4-hydroxy-2-butanone (4-OH-2B)] may be present in an amount lower than or equal to 2% by weight, preferably in an amount lower than or equal to 1% by weight, based on the total weight of said aqueous solution;

any products derived from the decomposition of the bio-1,3-butanediol [for example, 3-buten-2-one, 2-buten-1-ol (cis and trans isomers), 3-buten-1-ol, 3-buten-2-ol] may be present in an amount lower than or equal to 0.01% by weight, preferably lower than or equal to 0.005% by weight, based on the total weight of said aqueous solution;

any sugars (for example, glucose) may be present in an amount lower than or equal to 0.001 g/l, preferably lower than or equal to 0.0005 g/l.

For the purpose of the present description and of the following claims, the term "bio-1,3-butanediol" indicates that said 1,3-butanediol is synthesised from one or more species or strains of living organisms including, preferably, strains of bacteria, yeasts, fungi and other organisms. In general, said fermentation broth may be derived from fermentation of commercially available sugars, or deriving from renewable sources, carried out in a suitable culture medium, in the presence of at least one microorganism genetically modified to produce 1,3-butanediol. Generally, said microorganism is genetically modified by introducing one or more exogenous genes which code for compounds belonging to the enzyme pathway directed towards the production of 1,3-butanediol. Optionally, said microorganism may further contain gene disruption to optimise the flow of carbon through the desired pathway for the production of 1,3-butanediol. Said renewable sources are generally biomasses of plant origin: for this purpose it is possible to use, for example, sugar cane and beet as sources of sugar (for example, glucose, arabinose, xylose, sucrose), or maize and potato as a source of starch and, thus, of dextrose.

Looking to the future, however, non-food biomasses are of higher interest, such as maize stalks, cereal straws, arundo, thistle stalks, guayule bagasse etc., which may provide sugars through breakdown of the cellulose and hemicellulose. Generally, the biomass of plant origin is subjected to chemical and/or enzymatic hydrolysis to obtain substrates which may subsequently be processed biocatalytically to obtain the chemical products of interest. Said substrates includes mixtures of carbohydrates, as well as aromatic compounds and other products derived from the cellulose, hemicellulose and lignin present in the biomass. The carbohydrates obtained from the hydrolysis of said biomass are a mixture rich in sugars having 5 and 6 carbon atoms and include, for example, sucrose, glucose, xylose, arabinose, galactose, mannose and fructose, which will be used in the fermentation. Further details relating to the aforementioned processes for the synthesis of 1,3-butanediol may be found, for example, in American patent applications US 2010/330635, US 2012/329113, US 2013/066035, US 2013/109064, incorporated herein by reference.

To purify the bio-1,3-butanediol from the fermentation broth, it is first desirable to separate the cell biomass, as well as the cell debris, and the contaminants having a relatively high molecular weight from said fermentation broth. Processes useful for separating the cell biomass and other compounds in the form of particles from liquids, such as filtration, centrifugation, are known in the art.

In a preferred embodiment of the present invention, said step (a) may comprise the following steps:
($a_{1a}$) microfiltration; and
($a_2$) nanofiltration.

In a further preferred embodiment of the present invention, said step (a) may comprise the following steps:
($a_{1b}$) centrifugation; and
($a_2$) nanofiltration.

In a preferred embodiment of the present invention, said microfiltration step ($a_{1a}$) may be carried out by membranes having a mean pore diameter ranging from 0.01 µm to 1.0 µm, preferably ranging from 0.02 µm to 0.08 µm.

In a preferred embodiment of the present invention, said microfiltration step ($a_{1a}$) may be carried out operating at a transmembrane pressure ranging from 0.1 bar to 8 bar, preferably ranging from 1 bar to 5 bar, said transmembrane pressure being defined as the average pressure between the pressure measured upstream and the pressure measured downstream of the microfiltration module.

In a preferred embodiment of the present invention, said microfiltration step ($a_{1a}$) may be carried out at a temperature ranging from 20° C. to 90° C., preferably ranging from 40° C. to 70° C., more preferably at the fermentation temperature.

In a preferred embodiment of the present invention, said microfiltration step ($a_{1a}$) may be carried out by ceramic membranes which are submerged or in a cross flow configuration or in a dynamic cross flow configuration, or by flat or hollow-fibre polymer membranes which are submerged or in a cross flow configuration.

Examples of membranes which may be used for the purpose of the present invention and which are commercially available are the "Hydrosart® Microfiltration Cassettes" products from Sartorius, or the Ceram Inside® products from Tami, or the Schumasiv™ or Membralox® products from Pall, or the Microza products from the Asahi Kasei Corporation.

At the end of said microfiltration step ($a_{1a}$), a permeate is obtained comprising bio-1,3-butanediol, water and residual impurities (for example, sugars, other organic impurities, salts) which may be sent to a nanofiltration step ($a_2$) as described above, or else directly to the step (b) of treatment with ion-exchange resins, as well as a retentate comprising the cell biomass and any cell debris. Said retentate may be dried and disposed of in landfill or incinerated, or else may be sent directly to a water treatment plant.

In a preferred embodiment of the present invention, said centrifugation step ($a_{1b}$) may be carried out at a temperature ranging from 20° C. to 90° C., preferably ranging from 25° C. to 70° C., more preferably at room temperature (25° C.).

In a preferred embodiment of the present invention, said centrifugation step ($a_{1b}$) may be carried out operating at a centrifugal feed rate ranging from 50 l/h to 1000 l/h, preferably ranging from 90 l/h to 500 l/h.

In a preferred embodiment of the present invention, said centrifugation step ($a_{1b}$) may be carried out at a rotation speed ranging from 2000 rpm to 50000 rpm, preferably ranging from 3000 rpm to 9000 rpm.

For the purpose of the present invention, said centrifugation step ($a_{1b}$) may be carried out in any type of centrifuge known in the art; in particular, a disc centrifuge with automatic panel ejection has been used, model CA21-P from Andritz.

At the end of said centrifugation step ($a_{1b}$), a lighter aqueous phase (supernatant) is obtained comprising bio-1,3-butanediol, water and residual impurities (for example, sugars, other organic impurities, salts) which may be sent to a nanofiltration step ($a_2$) as described above, or else directly to the step (b) of treatment with ion-exchange resins, as well as a second heavier aqueous phase (precipitate) comprising the cell biomass and any cell debris. Said second aqueous phase (precipitate) may be dried and disposed of in landfill or incinerated, or else may be sent directly to a water treatment plant.

In a preferred embodiment of the present invention, said nanofiltration step ($a_2$) may be carried out by nanofiltration membranes having a "molecular weight cut-off" (MWCO) ranging from 100 daltons to 500 daltons, preferably ranging from 120 daltons to 400 daltons.

In a preferred embodiment of the present invention, said nanofiltration step ($a_2$) may be carried out by nanofiltration membranes having a maximum operating temperature ranging from 15° C. to 100° C., preferably ranging from 20° C. to 80° C.

In a preferred embodiment of the present invention, said nanofiltration step ($a_2$) may be carried out operating at a transmembrane pressure ranging from 10 bar to 50 bar, preferably ranging from 20 bar to 40 bar, said transmembrane pressure being defined as the average pressure between the pressure measured upstream and the pressure measured downstream of the nanofiltration module.

The aforementioned hydrophilic nanofiltration membranes may be in the form of flat sheets, hollow fibres, tubular membrane, spiral-wound membranes, or in other beneficial forms.

Nanofiltration membranes which may advantageously be used for the purpose of the present invention are the products known by the trade names DK Series from GE Power & Water, or SR3D™ Membrane from Koch Membrane Systems.

At the end of said nanofiltration step ($a_2$), a permeate is obtained comprising bio-1,3-butanediol, water and residual impurities (for example, salts, acids) which is sent to the step (b) of treatment with ion-exchange resins, as well as a retentate comprising compounds having high steric hindrance (for example, proteins, divalent salts). Said retentate may be sent directly to a water treatment plant.

In a preferred embodiment of the present invention, said step (b) of treatment with ion-exchange resins may comprise two steps:
($b_1$) anion exchange step;
($b_2$) cation exchange step.

In a preferred embodiment of the present invention, said step ($b_1$) may be carried out by means of a column containing a weak anionic resin.

Weak anionic resins which may advantageously be used for the purpose of the present invention are the products known by the trade names Dowex™ Monosphere™ 77 from Dow Chemical, or Diaion® WA30 from Mitsubishi Chemical Corporation.

In a preferred embodiment of the present invention, said step ($b_2$) may be carried out by means of a column containing a strong cationic resin.

Strong cationic resins which may advantageously be used for the purpose of the present invention are the products known by the trade names Dowex™ Monosphere™ 88 from Dow Chemical, or Amberlite™ MB150 from Rohm & Haas Resins.

In a preferred embodiment of the present invention, said steps ($b_1$) and ($b_2$) may be carried out at a temperature ranging from 15° C. to 50° C., preferably ranging from 20° C. to 45° C.

In a preferred embodiment of the present invention, said steps ($b_1$) and ($b_2$) may be carried out at a flow rate [litres of product obtained in step (a) per hour] ranging from 2 BV/h to 4 BV/h, preferably ranging from 2.5 BV/h to 3.5 BV/h (BV="Bed Volume"=volume of resin per single column).

In a preferred embodiment of the present invention, the product obtained from said steps ($b_1$) and ($b_2$) may have a residual conductivity ranging from 0.1 µS/cm to 100 µS/cm, preferably ranging from 0.5 µS/cm to 15 µS/cm.

In a preferred embodiment of the present invention, the product obtained in step (a) may be fed to step ($b_1$) and subsequently to step ($b_2$), or may be fed to step ($b_2$) and subsequently to step ($b_1$).

At the end of said step (b) of treatment with ion-exchange resins, an aqueous solution is obtained comprising bio-1,3-butanediol, water, light organic compounds (for example, ethanol), heavy organic compounds [for example, 4-hydroxy-2-butanone (4-OH-2B)], unconverted sugars and any unremoved salts. Said aqueous solution is sent to the first evaporation step (c).

At the end of said step (b), the columns containing the ion-exchange resins used in the aforementioned steps ($b_1$) and ($b_2$) are subjected to regeneration by means of solutions of acids or bases, operating in accordance with processes known in the art.

In a preferred embodiment of the present invention, said first evaporation step (c) may be carried out at a temperature ranging from 30° C. to 100° C., preferably ranging from 40° C. to 70° C.

In a preferred embodiment of the present invention, said first evaporation step (c) may be carried out at a pressure ranging from 5 mbar to 100 mbar, preferably ranging from 10 mbar to 80 mbar.

Any type of evaporator known in the art may advantageously be used for the purpose of said step (c). Specific examples of evaporators which may advantageously be used are: rotary evaporators, "natural circulation" evaporators in which the evaporation is brought about by the movements caused simply by boiling, kettle evaporators, evaporators in which the evaporation is brought about by means of forced circulation in which the speed and turbulence are incremented using a circulation pump (forced-circulation evaporators), ME-EV evaporators (multi-effect evaporators), single-stage or multi-stage evaporators, single-effect evaporators, STV evaporators (short-tube vertical evaporators), LTV evaporators (long-tube vertical evaporators), basket-type evaporators, horizontal-tube evaporators, falling film evaporators, wiped film evaporators, flash evaporators, multi-stage flash evaporators, and the like. Preferably, an ME-EV evaporator (multi-effect evaporator) may be used in said step (c).

At the end of said first evaporation step (c), a concentrated solution is obtained comprising bio-1,3-butanediol, water, heavy organic compounds [for example, 4-hydroxy-2-butanone (4-OH-2B)], unconverted sugars and any unremoved salts, which is sent to the second evaporation step (d), as well as an aqueous phase comprising primarily water and traces of ethanol and of bio-1,3-butanediol, which may be recycled to one of the following steps: ($a_{1a}$) microfiltration, ($a_{1b}$) centrifugation, ($a_2$) nanofiltration, (b) treatment with ion-exchange resins. Alternatively, said aqueous phase may be sent directly to a water treatment plant.

In a preferred embodiment of the present invention, said second evaporation step (d) may be carried out at a temperature ranging from 30° C. to 150° C., preferably ranging from 40° C. to 130° C.

In a preferred embodiment of the present invention, said second evaporation step (d) may be carried out at a pressure ranging from 1 mbar to 100 bar, preferably ranging from 8 mbar to 80 mbar.

Any type of evaporator known in the art may advantageously be used for the purpose of the aforementioned step (d). Specific examples of evaporators which may advantageously be used are those reported above. Preferably, a wiped-film evaporator may be used in said step (d).

At the end of said second evaporation step (d), a concentrated solution is obtained comprising bio-1,3-butanediol, water and traces of heavy organic compounds [for example, 4-hydroxy-2-butanone (4-OH-2B)], of unconverted sugars and of any unremoved salts, which is sent to the third evaporation step (e), as well as an aqueous phase comprising primarily water, organic compounds having a boiling point lower than that of bio-1,3-butanediol, and traces of bio-1,3-butanediol which may be sent directly to a water treatment plant.

In a preferred embodiment of the present invention, said third evaporation step (e) may be carried out at a temperature ranging from 30° C. to 150° C., preferably ranging from 40° C. to 130° C.

In a preferred embodiment of the present invention, said third evaporation step (e) may be carried out at a pressure ranging from 5 mbar to 100 bar, preferably ranging from 8 mbar to 80 mbar.

Any type of evaporator known in the art may advantageously be used for the purpose of the aforementioned step (e). Specific examples of evaporators which may advantageously be used are those reported above. Preferably, a wiped-film evaporator may be used in said step (e).

At the end of said third evaporation step (e), two phases are obtained:
  an aqueous phase comprising purified bio-1,3-butanediol;
  an organic phase comprising any organic compounds having a boiling point higher than that of bio-1,3-butanediol and traces of unpurified bio-1,3-butanediol, of unconverted sugars and of any unremoved salts.

Further details on the types of evaporators used may be found for example in "Process Heat Transfer", Donald Q. Kern, McGraw-Hill (1950), Chapter 14, Evaporator, pp. 375-510; Perry's Chemical Engineers' Handbook, McGraw-Hill ($7^{th}$ ed.—1997), Section 11, pp. 108-118.

It should be noted that, in said evaporation steps (c), (d) and (e), the evaporation rate will be at a maximum at the start of the evaporation and will proceed to decrease until it is zero at the end of the evaporation.

As stated above, the bio-1,3-butanediol recovered at the end of said step (e) may advantageously be used in a process for the production of bio-1,3-butadiene.

Therefore, a further subject matter of the present invention is a process for the preparation of bio-1,3-butadiene comprising
  feeding a mixture (i) containing bio-1,3-butanediol, obtained according to the process above described, to a first reactor containing at least one dehydration catalyst, obtaining a stream (ii) comprising alkenols, water and, optionally, unreacted impurities and/or unreacted bio-1,3-butanediol, exiting from said first reactor;
  optionally, feeding said stream (ii) to a first purification section, obtaining:
  a stream (iii) comprising alkenols, water and, optionally, impurities;
  a stream (iv) comprising water and, optionally, impurities and/or unreacted bio-1,3-butanediol; and, optionally
  a stream (v) comprising impurities;
  feeding said stream (iii) and/or said stream (iv) to a second reactor containing at least one dehydration catalyst, obtaining a stream (vi) comprising bio-1,3-butadiene, water and, optionally, impurities and/or unreacted alkenols, exiting from said second reactor;
  feeding said stream (vi) to a second purification section, obtaining:
  a stream (vii) comprising pure bio-1,3-butadiene;
  a stream (viii) comprising water and, optionally, unreacted alkenols; and, optionally
  a stream (ix) comprising impurities.

For the purpose of the present invention, said process for the preparation of bio-1,3-butadiene may advantageously be carried out as described in American patent application US 2017/313633, in the name of the Applicant, incorporated herein by reference.

However, it should be noted that said bio-1,3-butanediol may advantageously be used for the preparation of bio-1,3-butadiene in accordance with any of the processes known in the art operating as described, for example, in international patent application WO 2015/173780, in American patent applications US 2018/0002250, US 2018/0002249, in the name of the Applicant, incorporated herein by reference.

As stated above, a further subject matter of the present invention is also the use of said bio-1,3-butanediol as a monomer or as an intermediate in the production of elastomers and (co)polymers.

The present invention will now be illustrated in higher detail by way of a form of implementation, with reference to FIG. 1 and FIG. 2 below reported.

DETAILED DESCRIPTION OF THE DISCLOSURE

Figure 1:
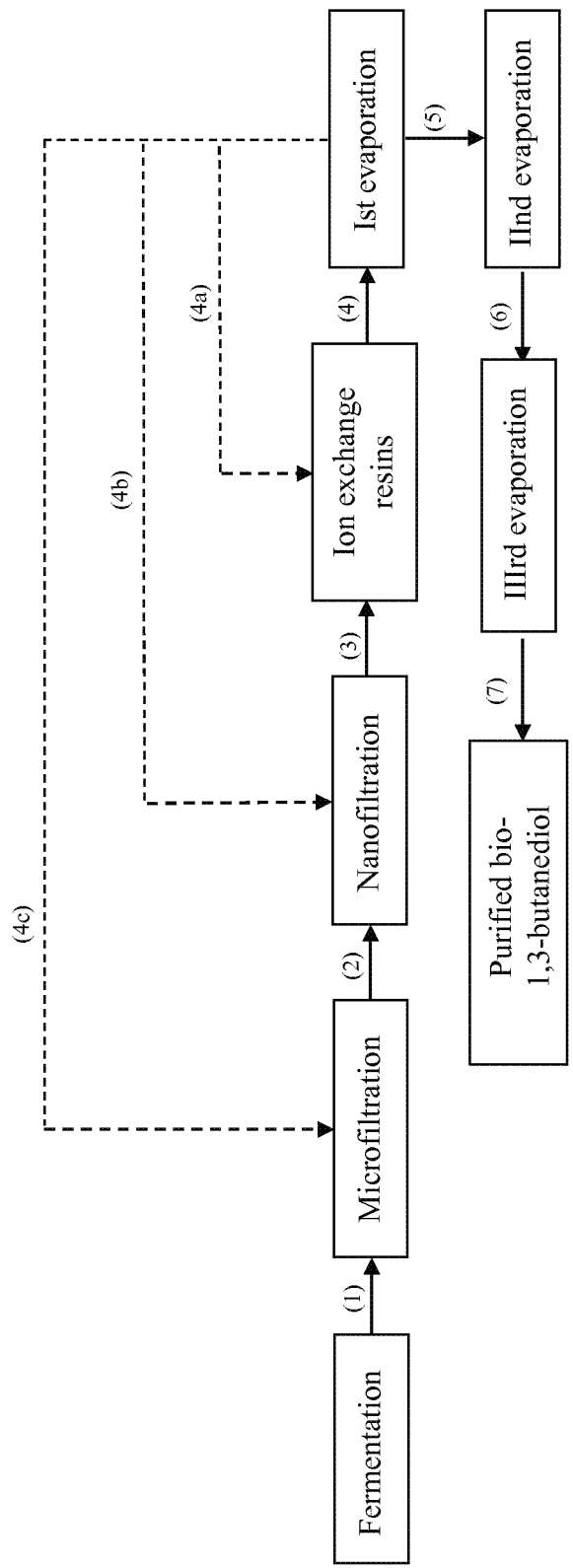
FIG. 1 shows a process according to the present invention.

In this context, a fermentation broth (1) comprising bio-1,3-butanediol and water, said fermentation broth preferably being derived from fermentation of sugars obtained from biomass, is sent to the microfiltration step, obtaining a permeate (2) comprising bio-1,3-butanediol, water and residual impurities (for example, sugars, other organic impurities, salts) which is sent to the nanofiltration step, as well as a retentate (not shown in FIG. 1) comprising the cell biomass and any cell debris which may be dried and disposed of in landfill or incinerated, or else may be sent directly to a water treatment plant. At the end of said nanofiltration step, a permeate (3) is obtained comprising bio-1,3-butanediol, water and residual impurities (for example, salts) which is sent to the step of treatment with ion-exchange resins, as well as a retentate (not shown in FIG. 1) comprising compounds having high steric hindrance (for example, proteins, divalent salts) which may be sent directly to a water treatment plant. Said permeate (3) is thus subjected to the step of treatment with ion-exchange resins, namely to a treatment in a column containing a weak anionic resin followed by a treatment in a column containing a strong cationic resin, or vice versa (not shown in FIG. 1), obtaining an aqueous solution (4) comprising bio-1,3-butanediol, water, light organic compounds (for example, ethanol), heavy organic compounds [for example, 4-hydroxy-2-hutanone (4-OH-2B)], unconverted sugars and any unremoved salts. Said aqueous solution (4) is sent to the first evaporation step, obtaining a concentrated solution (5) comprising bio-1,3-butanediol, water, heavy organic compounds [for example, 4-hydroxy-2-butanone (4-OH-2B)], unconverted sugars and any unremoved salts which is sent to the second evaporation step, as well as an aqueous phase (not shown in FIG. 1) comprising primarily water and traces of ethanol and of bio-1,3-butanediol which may be recycled to one of the following steps: ($a_{1a}$) microfiltration (4c), ($a_2$) nanofiltration (4b), (b) treatment with ion-exchange resins. (4a) (shown in dashed lines in FIG. 1). From said second evaporation step, a concentrated solution (6) is obtained comprising bio-1,3-butanediol, water and traces of heavy organic compounds [for example, 4-hydroxy-2-butanone (4-OH-2B)], of unconverted sugars and of any unremoved salts which is sent to the third evaporation step, as well as an aqueous phase (not shown in FIG. 1) comprising primarily water, organic compounds having a boiling point lower than that of bio-1,3-butanediol and traces of bio-1,3-butanediol which may be sent directly to a water treatment plant. From said third evaporation step, two phases are obtained: an aqueous phase (7) comprising purified bio-1,3-butanediol as well as an organic phase (not shown in FIG. 1) comprising any organic compounds having a boiling point higher than that of bio-1,3-butanediol and traces of unpurified bio-1,3-butanediol, of unconverted sugars and of any unremoved salts.

Figure 2:
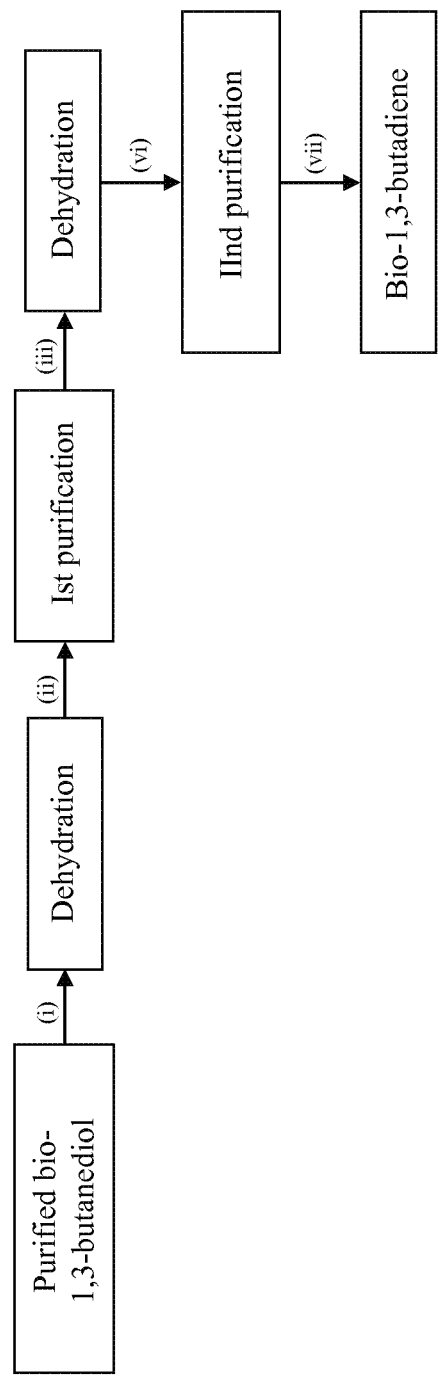
FIG. 2 shows a form of implementation of the process for the preparation of bio-1,3-butadiene according to the present disclosure.

In FIG. 2, the mixture (i) containing bio-1,3-butanediol obtained in accordance with the process object of the present invention is fed to a first reactor containing at least one dehydration catalyst, obtaining a stream (ii) comprising alkenols, water, and optionally impurities and/or unreacted bio-1,3-butanediol exiting from said first reactor; said stream (ii) is fed to a first purification section, obtaining a stream (iii) comprising alkenols, water, and, optionally, impurities, a stream (iv) comprising water and, optionally, impurities and/or unreacted bio-1,3-butanediol (not shown in FIG. 2), and a stream (v) comprising impurities (not shown in FIG. 2); said stream (iii) is fed to a second reactor containing at least one dehydration catalyst, obtaining a stream (vi) comprising bio-1,3-butadiene, water and, optionally, impurities and/or unreacted alkenols exiting from said second reactor, which is fed to a second purification section, obtaining a stream (vii) comprising pure bio-1,3-butadiene, a stream (viii) comprising water and, optionally, unreacted alkenols (not shown in FIG. 2) and, optionally, a stream (ix) comprising impurities (not shown in FIG. 2).

For better understanding of the present invention and for putting it into practice, illustrative, non-limiting examples thereof are reported hereinafter.

Example 1

Purification of Bio-1,3-Butanediol

For this purpose, a model fermentation broth was used containing bio-1,3-butanediol (referred to hereinafter as bio-1,3-BDO for simplicity) having the average composition reported in Table 1.

TABLE 1

Composition of model fermentation broth containing bio-1,3-BDO

| Compounds* | | Amount |
| --- | --- | --- |
| Bio-1,3-BDO | (g/l) | 70-95 |
| Cell biomass | (g/l) | 20 |
| By-products (ethanol, acetic acid, 4-hydroxy-2-butanone, proteins) | (g/l) | 20-35 |
| Residual salts | (g/l) | <10 |
| Residual glucose | (g/l) | <1 |

*balance made up by water.

The content of sugars and organic acids, as well as bio-1,3-butanediol, in diluted solutions (i.e. in aqueous solutions having a concentration of 1,3-BDO<150 g/l) was determined by high-performance liquid chromatography (HPLC), using a Waters 2690 Alliance "module system" chromatograph equipped with a binary pump, degasser, auto-sampler and compartment for the thermostated column. The column used is Phenomenex Rezex ROA-Organic Acid $H^+$, having dimensions 300×7.8 mm, at 45° C., in isocratic with aqueous solution 0.005 N sulphuric acid ($H_2SO_4$) at 0.6 ml/min flow rate. Two detectors were used: a Waters 2487 UV/Vis dual absorbance detector (DAD) and a Waters 2410 refractive index detector (RID).

The fermentation broth reported in Table 1, was divided into three separate batches, i.e. "batch 03", "batch 04" and "batch 05", and was purified operating as follows.

Removal of Cell Biomass by Microfiltration

To remove the cell biomass, the fermentation broth, i.e. "batch 04" and "batch 05", was sent to a microfiltration module comprising a Membralox® ceramic membrane in a cross flow configuration having a mean pore diameter of 0.05 μm. Said microfiltration module was subdivided into 19 channels having a diameter of 6 mm and a total filtering area of 0.36 $m^2$. During the test, it was attempted to maintain a flow speed of 4-5 m/s within the membrane, so as to limit the fouling thereof and reach a concentration factor [volume concentration ratio (VCR)], defined as the ratio between the volume of fermentation broth fed in and the volume of permeate obtained, higher than 5, preferably ranging from 6 to 10: further data relating to the operating conditions under which the microfiltration was carried out are reported in Table 2. At the end of the microfiltration, a permeate was obtained comprising bio-1,3-BDO, water and residual impurities (for example, sugars, other organic impurities, salts) which was sent to a nanofiltration module operating as described below, as well as a retentate comprising cell biomass and any cell debris which was dried and disposed of in landfill: the amount of bio-1,3-BDO recovered is also reported in Table 2.

Removal of Cell Biomass by Centrifugation

To remove the cell biomass, the fermentation broth, i.e. "batch 03", was subjected to centrifugation using a disc centrifuge with automatic panel ejection, model CA 21-P (Andritz), operating under the following conditions:

feed rate: 100 litres/h;
panel ejection interval: 5 minutes;
ejection method: water injection;
rotational speed: 8000 rpm;
temperature: room temperature (25° C.).

Further data relating to the operating conditions under which the centrifugation was carried out are reported in Table 2. At the end of the centrifugation, a first lighter aqueous phase (supernatant) was obtained comprising bio-1,3-BDO, water and residual impurities (for example, sugars, other organic impurities, salts) which was sent to a nanofiltration module operating as described below, as well as a second heavier aqueous phase (precipitate) comprising the cell biomass and any cell "debris" which was dried and disposed of in landfill: the amount of bio-1,3-BDO recovered is also reported in Table 2.

TABLE 2

Operating conditions for the microfiltration ("batch 04" and "batch 05") and centrifugation ("batch 03")

|  |  | "batch 03" Centrifugation | "batch 04" Microfiltration | "batch 05" Microfiltration |
|---|---|---|---|---|
| Fermentation broth fed in | (kg) | 123 | 138.2 | 90 |
| Average permeate flow rate | (kg/m$^2$/h) | 100$^{(1)}$ | 72.3 | 107.2 |
| Average permeate temperature | (° C.) | ≈40$^{(2)}$ | 52.8 | 57.2 |
| Final VCR | — | — | 6.2 | 9.5 | 7.6 |
| Transmembrane pressure | (bar) | — | 3 | 3 |
| Bio-1,3-BDO end balance $^{(3)}$ | (%) | 98 | 98 | 98 |
| Bio-1,3-BDO recovered | (kg) | 6.3 | 12.4 | 5.5 |

$^{(1)}$ flow rate of the feed pump;
$^{(2)}$ non-thermostated system;
$^{(3)}$ amount of bio-1,3-BDO exiting from the centrifuge or from the microfiltration module divided by the amount of bio-1,3-BDO entering the centrifuge or the microfiltration module × 100.

Nanofiltration

To remove water and residual impurities (for example, sugars, other organic impurities, salts), the nanofiltration step was carried out.

The permeate exiting the microfiltration module, derived from "batch 04" and "batch 05", was fed to a nanofiltration module containing a spiral-wound membrane, while the first aqueous phase (supernatant) exiting the centrifuge, derived from "batch 03", was fed to a vibratory nanofiltration system, referred to as a VSEP (vibratory shear-enhanced processing unit—New Logic Research Inc.). Both systems were provided with GE DK membranes (Koch Membrane Systems) having a molecular weight cut-off "(MWCO) ranging from 150 daltons to 300 daltons.

Further data relating to the operating conditions under which the nanofiltration was carried out are reported in Table 3. At the end of the nanofiltration, a permeate was obtained comprising bio-1,3-BDO, water and residual impurities (for example salts, acids) which was sent to the treatment with ion-exchange resins, as well as a retentate comprising compounds having high steric hindrance (for example, proteins, divalent salts) which was dried and disposed of in landfill: the amount of bio-1,3-BDO recovered is also reported in Table 3.

TABLE 3

Operating conditions for the nanofiltration ("batch 03", "batch 04" and "batch 05")

|  |  | "batch 03" VSEP | "batch 04" Spiralled | "batch 05" Spiralled |
|---|---|---|---|---|
| Permeate fed in | (kg) | — | 200 | 166 |
| First aqueous phase fed in | (kg) | 121 | — | — |
| Initial conductivity | (mS/cm) | 15 | 8 | 11 |
| Final VCR |  | 6.8 | 6.2 | 9.6 |
| Average permeate flow rate | (kg/h/m$^2$) | 16 | 43.3 | 30.4 |
| Average temperature | (° C.) | 49 | 41 | 42 |
| Final conductivity | (mS/cm) | 13 | 4 | 4 |
| Transmembrane pressure | (bar) | 30.7 | 26 | 25.5 |
| Bio-1,3-BDO end balance$^{(1)}$ | (%) | 96 | 101 | 101 |
| Bio-1,3-BDO recovered | (kg) | 5.6 | 11.4 | 5.4 |

$^{(1)}$ amount of bio-1,3-BDO exiting from the nanofiltration module divided by the amount of bio-1,3-BDO entering the nanofiltration module × 100.

Treatment with Ion-Exchange Resins

To remove residual impurities (for example, salts, acids), the step of treatment with ion-exchange resins was carried out.

For this purpose, the permeate exiting from the nanofiltration module, derived from "batch 03", was divided into two aliquots, referred to as "batch 03-1" and "batch 03-2" before being sent to the step of treatment with ion-exchange resins.

The permeate exiting the nanofiltration module, derived from "batch 03" (i.e. "batch 03-1" and "batch 03-2"), from "batch 04" and from "batch-05", was fed to a system from treatment with ion-exchange resins.

The system was composed of two transparent polyvinylchloride columns (PVC-U—GF Piping System) having the following dimensions: diameter=151 mm, height=1200 mm. Said two columns were connected in series, filled with ion-exchange resins: the first column was filled with a strong cationic resin (Dowex™ Monosphere™ 88—Dow Chemical), while the second column was filled with a weak anionic resin (Dowex™ Monosphere™ 77—Dow Chemical).

The purpose of the operation was to obtain a conductivity of the product exiting from the second column<15 μS/cm, and if the exiting product had a higher conductivity said product was fed to said system again after regeneration of the resin.

Said step of treatment with ion-exchange resins was carried out at room temperature (25° C.), while the flow rate was 3.3 BV/h using a metering pump (solenoid-diaphragm metering pump Delta® 4—ProMinent).

Further data relating to the operating conditions under which the step of treatment with ion-exchange resins was carried out are reported in Table 4. At the end of said treatment with ion-exchange resins, an aqueous solution was obtained comprising bio-1,3-BDO, water, light organic compounds (for example, ethanol), heavy organic compounds [for example, 4-hydroxy-2-butanone (4-OH-2B)], unconverted sugars and any unremoved salts which was fed to a rotary evaporator (first evaporation step): the amount of bio-1,3-BDO recovered is also reported in Table 4.

TABLE 4

Operating conditions for treatment with ion-exchange resins ("batch 03-1", "batch 03-2", "batch 04" and "batch 05")

|  |  | "batch 03-1" | "batch 03-2" | "batch 04" | "batch 05" |
|---|---|---|---|---|---|
| Permeate fed in | (kg) | 61 | 60 | 240 | 162 |
| "Bed Volume" | (L resin/column) | 6 | 12 | 12 | 12 |
| Permeate conductivity at the entering | (mS/cm) | 13 | 13 | 4 | 4 |

TABLE 4-continued

Operating conditions for treatment with ion-exchange resins ("batch 03-1", "batch 03-2", "batch 04" and "batch 05")

|  |  | "batch 03-1" | "batch 03-2" | "batch 04" | "batch 05" |
|---|---|---|---|---|---|
| Product conductivity at the exiting | (µS/cm) | 1.8 | 1.6 | 0.6 | 11.1 |
| Flow rate | (BV/h) | 3.3 | 3.3 | 3.3 | 3.3 |
| Bio-1,3-BDO end balance [1] | (%) | 100[2] |  | 98 | 94 |
| Bio-1,3-BDO recovered | (kg) | 2.9 | 2.6 | 11.2 | 4.9 |

[1] amount of bio-1,3-BDO exiting from the system for treatment with ion-exchange resins divided by the amount of bio-1,3-BDO entering the system for treatment with ion-exchange resins × 100;
[2] total of the amounts obtained from the treatment of "batch 03-1" and "batch 03-2" with ion-exchange resins.

First Evaporation

To eliminate the water and the light organic compounds (for example, ethanol), the aqueous solutions obtained from the step of treatment with ion-exchange resins were subjected to the first evaporation step.

The solutions obtained from the step of treatment with ion-exchange resins were thus fed to a Buchi Rotavapor® rotary evaporator, having a 20-litre loading ball flask, which was heated by immersion in a thermostated water bath. The solution was fed semi-continuously to the loading ball flask and the vapour phase was removed from the evaporator, obtaining a concentrated solution comprising bio-1,3-BDO, water, heavy organic compounds [for example, 4-hydroxy-2-butanone (4-OH-2B)], unconverted sugars and any unremoved salts which was sent to the second evaporation step, as well as an aqueous phase comprising primarily water and traces of ethanol and of bio-1,3-BDO which could be recycled to one of the following steps: ($a_{1a}$) microfiltration, ($a_{1b}$) centrifugation, ($a_2$) nanofiltration, (b) treatment with ion-exchange resins.

The conditions for said first evaporation step were as follows:

thermostated bath temperature: 60° C.;

pressure: 70 mbar-10 mbar.

The evaporation was considered complete at the end of the condensation of the vapours.

The concentrated solutions comprising bio-1,3-BDO were further purified as described in the examples below reported. In particular:

the concentrated solution originating from "batch 04" was divided into two aliquots, i.e. "batch 04-1" and "batch 04-2";

the concentrated solutions derived from "batch 03-2" and "batch 04-2" were further purified as described in Example 2 (invention) and in Example 5 (invention) respectively;

the concentrated solution derived from "batch 03-1" was further purified as described in Example 3 (comparative);

the concentrated solutions derived from "batch 05" and "batch 04-1" were further purified as described in Example 4 (comparative) and in Example 6 (comparative) respectively.

Example 2

Purification of Bio-1,3-BDO (Second and Third Evaporation) (Invention)

The second evaporation and third evaporation steps were carried out as reported below, under the operating conditions reported in Table 5.

For this purpose, the concentrated solution originating from the first evaporation step, i.e. "batch 03-2" (about 2.6 kg), was fed to a rotary evaporator (Laborota® 4003 control—Heidolph) with a 2-litre loading ball flask.

The heating was provided by immersing the loading ball flask in an oil bath equipped with a thermostat. The condenser was formed by a glass coil in the interior of which water and ethylene glycol (about 10%) circulated in a closed circuit. The cooling of the refrigerant fluid was provided by an air/liquid cryostat.

The test started under the operating conditions of the first evaporation step (i.e. 60° C. in the thermostated bath and pressure 70-30 mbar) until absence of evaporation from the sample was verified. Any aqueous phase recovered was discarded. Subsequently, the operating conditions adopted for the second evaporation step and for the third evaporation step are those reported in Table 5 (the evaporation was considered complete at the end of the condensation of the vapours): second evaporation (Step II) and third evaporation (Step III). The amounts of Phase (II) and Phase (III) recovered, as defined below, are also reported in Table 5.

TABLE 5

Operating conditions and phases recovered from "batch 03-2" IInd evaporation and IIIrd evaporation

| Phases | Weight (g) | Pressure (mbar) | Temperature (max) of oil bath (° C.) | Temperature of condenser (° C.) | Evaporation rate (g/h) |
|---|---|---|---|---|---|
| Phase II | 128 | 12-10 (Step II) | 110 (Step II) | 1 (Step II) | 36 (Step II) |
| Phase III | 2289 | 12-10 (Step III) | 125 (Step III) | 15 (Step III) | 264 (Step III) |

From Step II (second evaporation step) an aqueous phase was obtained comprising water, organic compounds having a boiling point lower than that of bio-1,3-BDO and traces of unpurified bio-1,3-BDO which was disposed of in landfill, as well as a concentrated solution (Phase II) comprising bio-1,3-BDO, water and traces of heavy organic compounds [for example, 4-hydroxy-2-butanone (4-OH-2B)], of unconverted sugars and of any unremoved salts which formed the feed to the third evaporation step (Step III).

From Step III (third evaporation step) an aqueous phase (Phase III) was obtained comprising purified bio-1,3-BDO, as well as an organic phase (Phase IV) comprising any organic compounds having a boiling point higher than that of bio-1,3-BDO and traces of unpurified bio-1,3-BDO, of unconverted sugars and of any unremoved salts.

Table 6 reports the gas chromatography (GC) analysis, carried out as described above in Example 1, of the recovered phases and of the feed ("batch 03-2").

TABLE 6

Composition of "batch 03-2" and of the recovered phases.

| | | "batch 03-2" | Phase III | Phase II | Phase IV |
|---|---|---|---|---|---|
| Composition[3] (%) | $H_2O$ | 8.8% | 1.5% | 43.0% | n.d. |
| | Bio-1,3-BDO | 88.0% | 96.6% | 34.9% | 408 g/l |
| | Bio-4-OH-2B[1] | 1.0% | 0.9% | 5.9% | n.d. |
| | Decomposition products of 1,3-BDO[2] | 0% | 0% | 0% | n.d. |
| | Glucose | 0.1 g/l | 0 g/l | 0 g/l | 15.5 g/l |

[1]bio-4-hydroxy-2-butanone;
[2]total of 3-buten-2-one, 2-buten-1-ol (cis and trans isomers), 3-buten-1-ol, 3-buten-2-ol;
[3]made up to 100 by other organic impurities not reported in Table 6.

Phase IV had a caramel appearances and was analysed only by high-performance liquid chromatography (HPLC), operating as described above in Example 1.

Meanwhile, for the analysis of Phase II and Phase III, an Agilent HP6890 gas chromatograph (GC) was used, equipped with a Split/Splitless injector on a Quadrex 007 FFAP column of 25 m length, 0.32 mm diameter, 1 µm film, the carrier used was helium at a speed of 50 cm/s, the detector was a flame detector. The determination was carried out using an internal standard with calibration curves for the known individual components. Karl Fischer titration (831 KF Coulometer Metrohm) was further used for the analysis of the water for Phase (III) (for Phase II, the amount of water was calculated by difference).

Phase III was subsequently fed to a dehydration system for the production of butenols, operating as described in Example 7 below reported.

Example 3

Purification of Bio-1,3-BDO (Comparative)

The concentrated solution originating from "batch 03-1", about 2.7 kg, was fed to a distillation column and processed in batches. The distillation was carried out using a 5-litre boiler and an adiabatic column (diameter=2 cm; height=60 cm) with Sulzer filling. During the distillation, the residual water and the organic compounds having a boiling point between that of water and that of bio-1,3-BDO were removed, whilst the high-boiling organic compounds, the residual salts and the unconverted sugar remained in the boiler: the fractions obtained from the distillation are reported in Table 7.

TABLE 7

Fractions distilled from batch 03-1
Distillation of batch 03-1

| Fraction | Weight (g) | Pressure (mbar) | Reflux ratio | Temperature (max) of vapours (° C.) | Temperature (max) of boiler (° C.) | Temperature of condenser (° C.) | Distillation rate (ml/h) |
|---|---|---|---|---|---|---|---|
| 1 | 93 | 67 | 5 | 36 | 134 | −5 | 15 |
| 2 | 16 | 50 | 5 | 69 | 127 | −5 | 3 |
| 3 | 28 | 50 | 5 | 88 | 127 | −5 | 5 |
| 4 | 14 | 50 | 5 | 116 | 128 | −5 | 4 |
| 5 | 11 | 50 | 5 | 121 | 128 | −5 | 2 |
| 6 | 13 | 50 | 5 | 124 | 128 | −5 | 3 |
| 7 | 2159 | 50 | 2 | 125 | 131 | −5 | 66 |
| 8 | 183 | 50 | 2 | 125 | 140 | −5 | 73 |

The fractions rich in bio-1,3-BDO are Fraction 7 and Fraction 8. However, all the fractions recovered ended up polluted by a molecule not present in the starting solution; said molecule was identified, using various analytic methods (FT-IR, GC-MS, GC, NMR), as the ketal which forms by reaction between bio-1,3-BDO and 3-buten-2-one (MVK), namely 2,4-dimethyl-2-vinyl-1,3-dioxane (DMV13Diox). In particular, the chromatogram obtained by gas chromatography analysis (GC), carried out as described above in Example 1, made it possible to observe the presence of a new peak in all the fractions, not present in the starting feed. The intensity of the peak in the various fractions ended up different, so different analytical techniques were used for the different fractions.

NMR analysis in solution, FT-IR and GC-MS identified said molecule as 2,4-dimethyl-2-vinyl-1,3-dioxane (DMV-13Diox). Said analyses were carried out as follows.

Spectroscopic NMR Analysis of a Sample of Fraction 1

The NMR spectra were recorded using a BrukerAvance 400 NMR tool in deuterated acetone solution. The signal of the $CH_3$ of the acetone, positioned at 2.05 ppm in the $^1$H-NMR spectrum and at 29.5 ppm in the $^{13}$C-NMR spectrum, was taken as a reference signal.

Various products were identified in the $^1$H-NMR spectrum (at different intensities: of these, the most abundant is characterised by the presence of a clearly recognisable vinyl group $CH_2$=CH— at 5.80, 5.32 and 5.29 ppm, corresponding in intensity to a set of signals attributable to $CH_2$—O— and CH—O, characterised, curiously, by very high coupling constants, this generally only being found in cyclic aliphatic systems). Said results made it possible to identify a ketal species, in particular, knowing the primary compounds of the fraction, of the DMV13Diox. All of the couplings were further appreciated only with the aid of a two-dimensional COSY $^1$H-$^1$H spectrum.

Mass Spectrum of a Sample of Fraction 7

Fraction 7 was analysed by gas chromatography-mass spectrometry (GC-MS) on a single-quadrupole spectrometer (Trace DSQ, Thermo), using the headspace method. The sample was measured in a headspace vial and was heated to 80° C. for about one hour. Subsequently, 1 ml of the gaseous phase supernatant on the liquid (area and vapours derived from the sample under examination) and was injected into the gas chromatograph by a method which makes it possible to separate the air (in excess) from the organic components. The analysis conditions used were as follows: temperature scheme of the gas chromatograph from 50° C. to 300° C. at 4° C./minute, injection in split mode, temperature of injector 280° C., transfer line 250° C. Mass spectra recorded from 35 daltons to 500 daltons in electronic ionisation (EI) mode.

Mass Spectrum (EI) for the Species at Retention Time 3.9 Minutes

Although the molecular ion is not visible, it may be assumed that there is a loss of methyl ($CH_3$) from the molecular ion to generate ion 127 (rel. abundance 22.5%) and a loss of 27 (allyl) for ion 115 (rel. abundance 80.9%). A molecular weight of 142 is thus assumed, which would confirm the hypothesis put forward on the basis of the NMR analysis reported above. Starting from the structure hypothesised from the NMR analysis, it would also be possible to explain the other fragment ions obtained in the EI-MS spectrum (indeed, the EI technique generally includes high fragmentation of the organic molecules, and thus makes it possible to reconstruct or confirm the structure). In particular:

the main ion 55 (rel. abundance 100%) could correspond to the species $CH_2=CHCHCH_3^{+*}$, ion 71 (rel. abundance 35.3%) species $CH_2=CHCHOCH_3^{+*}$.

Mass Spectrum (EI) for the Species at Retention Time 4.44 Minutes

Main ion 55 (rel. abundance 100%) species $CH_2=CHCHCH_3^{+*}$, ion 71 (rel. abundance 19.3%) species $CH_2=CHCHOCH_3^{+*}$.

Ion 127 (rel. abundance 32.5%) through loss of methyl from the molecular ion; loss of 27 (allyl) from the molecular ion for ion 115 (rel. abundance 11.9%).

FT-IR Spectrum of a Sample of Fraction 1

The FT-IR spectra of the samples, deposited on a KBr window, were acquired using a Nicolet Nexus FT-IR spectrometer with 64 scans and a resolution of 2 $cm^{-1}$.

The bands attributable to the vinyl groups of the product DMV13Diox were found at 3088 $cm^{-1}$ ($CH_2$ asymmetric stretching) at 985 $cm^{-1}$ and 916 $cm^{-1}$ (CH and $CH_2$ wagging), while the bands in the range 1200 $cm^{-1}$-1100 $cm^{-1}$ and at 962 $cm^{-1}$ are attributable to the asymmetrical and symmetrical stretching respectively of the C—O bond. Likewise from the product DMV13Diox, the vibrations of the C—O—C bond at 1050 $cm^{-1}$ and of the C=C double bond at 1640 $cm^{-1}$ could be identified.

Table 8 reports the gas chromatography (GC) analysis, carried out as described in Example 1, of the feed ("batch 03-1"), of Fraction 7 and Fraction 8 derived from the distillation of "batch 03-1" and of the boiler residue obtained at the end of the distillation.

TABLE 8

GC analysis of the fractions rich in bio-1,3-BDO

| | | "batch 03-1" | Fraction 7 | Fraction 8 | Boiler residue |
|---|---|---|---|---|---|
| Composition[3] (%) | $H_2O$ | 3.1% | 0.1% | 0.1% | n.d. |
| | Bio-1,3-BDO | 88.3% | 98.0% | 97.5% | 544 g/l |
| | Bio-4-OH-2B[1] | 1.6% | 0% | 0% | n.d. |
| | DMV13Diox[2] | 0% | 0.4% | 0.2% | n.d. |
| | Glucose | n.d. | 0 g/l | 0 g/l | 5.3 g/l |

[1]bio-4-hydroxy-2-butanone;
[2]2,4-dimethyl-2-vinyl-1,3-dioxane (expressed as percentage area based on the area of the peak for the bio-1,3-BDO);
[3]made up to 100 by other organic impurities not reported in Table 8.

The boiler residue had a caramel appearance and was analysed only by HPLC, operating as described in Example 1 above. Karl Fischer titration (831 KF Coulometer Metrohm) was further used for the analysis of the water for Fraction 7 and for Fraction 8.

Example 4

Purification of Bio-1,3-BDO (Comparative)

The solution originating from "batch 05", about 4.2 kg, was fed to a distillation column and processed in batches. The distillation was carried out using a 5-litre boiler and an adiabatic column (diameter=2 cm; height=60 cm) with Sulzer filling. During the distillation, the residual water and the organic compounds having a boiling point between that of water and that of bio-1,3-BDO were removed, while the high-boiling organic compounds, the residual salts and the unconverted sugar remained in the boiler; Table 9 reports the fractions obtained from the distillation.

TABLE 9

Fractions distilled from "batch 05"
Distillation of "batch 05"

| Fraction | Weight (g) | Pressure (mbar) | Reflux ratio | Vapour temperature (max) (° C.) | Boiler temperature (max) (° C.) | Condenser temperature (° C.) | Distillation rate (ml/h) |
|---|---|---|---|---|---|---|---|
| 1 | 956 | 35 | 3 | 22 | 95 | 1 | 6 |
| 2 | 158 | 10 | 5 | 70 | 105 | 1 | 27 |
| 3 | 142 | 10 | 15 | 74 | 94 | 1 | 9 |
| 4 | 122 | 10 | 15 | 77 | 95 | 1 | 9 |
| 5 | 111 | 10 | 15 | 73 | 96 | 1 | 9 |
| 6 | 3277 | 12 | 3 | 85 | 107 | 10 | 32 |
| 7 | 135 | 12 | 3 | 85 | 137 | 10 | 34 |

The fractions rich in 1,3-BDO are Fraction 6 and Fraction 7.

By reducing the pressure in the column, and thus the temperature of the system, formation of 3-buten-2-one (MVK) and of the corresponding ketal is avoided. However, in the last fraction distilled (Fraction 7), the presence of decomposition products of bio-1,3-BDO, which lead to a decrease in the yield of the distillation, is noted: Table 10 reports the gas chromatography analysis, carried out as described in Example 1 above, of the fractions rich in bio-1,3-BDO.

TABLE 10

GC analysis of the fractions rich in 1,3-BDO "batch 05".

| | | "batch 05" | Fraction 5 | Fraction 6 | Fraction 7 | Boiler residue |
|---|---|---|---|---|---|---|
| Composition[4] (%) | $H_2O$ | 4.3% | 0.6% | 0.3% | 0.9% | n.d. |
| | Bio-1,3-BDO | 91.3% | 96.5% | 98.2% | 97.9% | 266 g/l |
| | Bio-4-OH-2B[1] | 0.6% | 0% | 0% | 0% | n.d. |
| | DMV13Diox[2] | 0% | 0% | 0% | 0% | n.d. |
| | Decomposition products of 1,3-BDO[3] | 0% | 0% | 0.01% | 0.58% | n.d. |
| | Glucose | 0.2 g/l | 0 g/l | 0 g/l | 0 g/l | 7.6 g/l |

[1]bio-4-hydroxy-2-butanone;
[2]2,4-dimethyl-2-vinyl-1,3-dioxane (expressed as percentage area based on the area of the peak for bio-1,3-BDO);
[3]total of buten-2-one, 2-buten-1-ol (cis and trans isomers), 3-buten-1-ol, 3-buten-2-ol;
[4]made up to 100 by other organic impurities not reported in Table 10.

The boiler residue had a caramel appearance and was analysed only by HPLC, operating as described in Example 1 above. Karl Fischer titration (831 KF Coulometer Metrohm) was further used for the analysis of the water for Fraction 5, for Fraction 6 and for Fraction 7.

Fraction 6 of "batch 5" was subsequently fed to a dehydration system for the production of butenols, operating as described in Example 7 below.

Example 5

Purification of Bio-1,3-BDO (Second and Third Evaporation) (Invention)

The second and third evaporation steps were carried out as reported below, under the operating conditions reported in Table 11.

For this purpose, the concentrated solution originating from the first evaporation step, i.e. "batch 04-2" (about 6.8 kg), was fed to a rotary evaporator (Laborota® 4003 control—Heidolph) with a 2-litre loading ball flask.

The heating was provided by immersing the loading ball flask in an oil bath equipped with a thermostat. The condenser was formed by a glass coil in the interior of which water and ethylene glycol (about 10%) circulated in a closed circuit. The cooling of the refrigerant fluid was provided by an air/liquid cryostat.

The test started under the operating conditions of the first evaporation step (i.e. 60° C. in the thermostated bath and pressure 70-30 mbar) until absence of evaporation from the sample was verified. Any aqueous phase recovered was discarded. Subsequently, the operating conditions adopted for the second evaporation step and for the third evaporation step are those reported in Table 11 (the evaporation was considered complete at the end of the condensation of the vapours): second evaporation (Step II) and third evaporation (Step III). The amounts of Phase (II) and Phase (III) recovered, as defined below, are also reported in Table 11.

TABLE 11

Operating conditions and phases recovered from "batch 04-2"
IInd evaporation and IIIrd evaporation

| Phases | Weight (g) | Pressure (mbar) | Temperature (max) of oil bath (° C.) | Condenser temperature (° C.) | Evaporation rate (g/h) |
|---|---|---|---|---|---|
| Phase II | 464 (Step II) | 12-10 (Step II) | 110 (Step II) | 1 (Step II) | 28 (Step II) |
| Phase III | 6827 (Step III) | 12-10 (Step III) | 125 (Step III) | 15 (Step III) | 338 (Step III) |

From Step II (second evaporation step) an aqueous phase was obtained comprising water, organic compounds having a boiling point lower than that of bio-1,3-BDO and traces of unpurified bio-1,3-BDO which was disposed of in landfill, as well as a concentrated solution (Phase II) comprising bio-1,3-BDO, water and traces of heavy organic compounds (for example, 4-hydroxy-2-butanone), of unconverted sugars and of any unremoved salts which formed the feed to the third evaporation step (Step III).

From Step III (third evaporation step) an aqueous phase (Phase III) was obtained comprising purified bio-1,3-BDO, as well as an organic phase (Phase IV) comprising any organic compounds having a boiling point higher than that of bio-1,3-BDO and traces of unpurified bio-1,3-BDO, of unconverted sugars and of any unremoved salts.

Table 12 reports the gas chromatography (GC) analysis, carried out as described above in Example 1, of the recovered phases and of the feed ("batch 04-2").

TABLE 12

Composition of "batch 04-2" and of the recovered phases.

| | | "batch 04-2" | Phase III | Phase II | Phase IV |
|---|---|---|---|---|---|
| Composition[3] (%) | H₂O | 4.2% | 0.7% | 52.8% | n.d. |
| | Bio-1,3-BDO | 94.1% | 97.8% | 34.9% | 374 g/l |
| | Bio-4-OH-2B[1] | 1.1% | 0.8% | 5.9% | n.d. |
| | Decomposition products of 1,3-BDO[2] | 0% | 0% | 0% | n.d. |
| | Glucose | 0.4 g/l | 0 g/l | 0 g/l | 26.9 g/l |

[1]bio-4-hydroxy-2-butanone;
[2]total of 3-buten-2-one, 2-buten-1-ol (cis and trans isomers), 3-buten-1-ol, 3-buten-2-ol;
[3]made up to 100 by other organic impurities not reported in Table 12.

Phase IV had a caramel appearances and was analysed only by high-performance liquid chromatography (HPLC), operating as described above in Example 1.

Karl Fischer titration (831 KF Coulometer Metrohm) was further used for the analysis of the water for Phase (III) (for Phase II, the amount of water was calculated by difference).

Phase III was subsequently fed to a dehydration system for the production of butenols, operating as described in Example 7 below reported.

Example 6

Purification of Bio-1,3-BDO (Comparative)

The solution originating from "batch 04-1", about 4.05 kg, was fed to a distillation column and processed in batches. The distillation was carried out using a 5-litre boiler and an adiabatic column (diameter=2 cm; height=60 cm) with Sulzer filling. During the distillation, the residual water and the organic compounds having a boiling point between that of water and that of bio-1,3-BDO were removed, while the high-boiling organic compounds, the residual salts and the unconverted sugar remained in the boiler: Table 13 reports the fractions obtained from the distillation.

TABLE 13

Fractions distilled from "batch 04-1"
Distillation of "batch 04-1"

| Fraction | Weight (g) | Pressure (mbar) | Reflux ratio | Vapour temperature (max) (° C.) | Boiler temperature (max) (° C.) | Condenser temperature (° C.) | Distillation rate (ml/h) |
|---|---|---|---|---|---|---|---|
| 1 | 124 | 30 | 3 | 24 | 97 | −1 | 16 |
| 2 | 70 | 12 | 30 | 82 | 102 | 5 | 6 |
| 3 | 260 | 12 | 3 | 84 | 103 | 5 | 55 |
| 4 | 3446 | 12 | 3 | 86 | 110 | 5 | 53 |
| 5 | 26 | 12 | 3 | 84 | 118 | 10 | 45 |

The fractions rich in 1,3-BDO are Fraction 4 and Fraction 5.

By reducing the pressure in the column, and thus the temperature of the system, formation of 3-buten-2-one (MVK) and of the corresponding ketal is avoided. However, in the last fraction distilled (Fraction 5), the presence of decomposition products of bio-1,3-BDO, which lead to a decrease in the yield of the distillation, is noted: Table 14 reports the gas chromatography (GC) analysis, carried out as described in Example 1 above reported, of the fractions rich in bio-1,3-BDO and of the feed ("batch 04-1").

TABLE 14

GC analysis of fractions rich in 1,3-BDO "batch 04-1".

| | | "batch 04-1" | Fraction 3 | Fraction 4 | Fraction 5 | boiler residue |
|---|---|---|---|---|---|---|
| Composition[4] (%) | H₂O | 2.6% | 0.4% | 0.1% | n.d. | n.d. |
| | Bio-1,3-BDO | 95.5% | 97.5% | 99% | 99% | 536 g/l |
| | Bio-4-OH-2B[1] | 0.9% | 0.5% | 0% | 0% | n.d. |
| | DMV13Diox[2] | 0% | 0% | 0% | 0% | n.d. |
| | Decomposition products of 1,3-BDO[3] | 0% | 0.04% | 0% | 0.03% | n.d. |
| | Glucose | 0.1 g/l | 0 g/l | 0 g/l | 0 g/l | 1.2 g/l |

[1]bio-4-hydroxy-2-butanone;
[2]2,4-dimethyl-2-vinyl-1,3-dioxane (expressed as percentage area based on the area of the peak for bio-1,3-BDO);
[3]total of 3-buten-2-one, 2-buten-1-ol (cis and trans isomers), 3-buten-1-ol, 3-buten-2-ol;
[4]made up to 100 by other organic impurities not reported in Table 14.

The boiler residue had a caramel appearance and was analysed only by HPLC, operating as described in Example 1 above. Karl Fischer titration (831 KF Coulometer Metrohm) was further used for the analysis of the water for Fractions 3, 4 and 5.

Fraction 4 of "batch 04-1" was subsequently fed to a dehydration system for the production of butenols, operating as described in Example 7 below reported.

Table 15 reports the yields of Example 2 (invention) (Phase III of "batch 03-2"), Example 4 (comparative) (Fraction 6 of "batch 05"), Example 5 (invention) (Phase III of "batch 04-2") and Example 6 (comparative) (Fraction 4 of "batch 04-1"). The yields of Example 3 (comparative) are not reported, since the fractions rich in 1,3-BDO are polluted by 2,4-dimethyl-2-vinyl-1,3-dioxane (DMV13Diox) and are not sent to a dehydration system for the production of butenols.

TABLE 15

Yield and recovery rate of the fractions of Example 1 and Example 4 (invention), Example 3 and Example 5 (comparative)

| | Global mass balance | Global mass balance of bio-1,3-BDO | Recovery of fraction rich in bio-1,3-BDO | Total recovery rate (g/h) | Bio-1,3-BDO recovery rate (g/h) |
|---|---|---|---|---|---|
| Example 2 (invention) ("batch 03-2") | 100% | 99% | 97% | 139 | 264 |
| Example 4 (comparative) ("batch 05") | 99% | 99% | 84% | 24 | 32 |
| Example 5 (invention) ("batch 04-2") | 101% | 99% | 96% | 192 | 338 |
| Example 6 (comparative) ("batch 04-1") | 100% | 97% | 88% | 44 | 53 |

The total recovery rate was calculated as the total of the recovered phases or fractions (g) divided by the overall hours of testing (h), counted from the first condensed drop removed. The bio-1,3-BDO recovery rate was calculated as the amount of purified phase fraction recovered (g) divided by the hours to purify this individual phase or fraction (h), counted from the first condensed drop removed of said phase or fraction.

From the data reported in Table 15, it may be seen that Example 2 and Example 5 (invention) end up having a higher yield (i.e. recovery of phase or fraction rich in bio-1,3-BDO) than Example 4 and Example 6 (comparative), and the bio-1,3-BDO recovery rate from the phase or fraction used ends up much higher.

Example 7

Production of Bio-Butenols from Bio-1,3-BDO

The purified 1,3-BDO obtained in Example 2 (invention) (Phase III of "batch 03-2") and the purified bio-1,3-BDO obtained in Example 4 (comparative) (Fraction 6 of "batch 05") were subjected to catalytic dehydration, operating as follows.

For this purpose, the catalysts A and B were first synthesised, operating as follows.

Synthesis of Catalyst A

In a glass beaker, provided with magnetic bar stirrer, was prepared a solution of 870 g of cerium nitrate hexahydrate in 4200 g water, by vigorous stirring, at room temperature (25° C.). The solution obtained was transferred into a glass reactor, equipped with stirring rod in the form of a bar, and was kept under stirring for 15 minutes. To the solution obtained, kept under stirring, were added, by peristaltic pump, 790 g of an aqueous solution at 15% of ammonium hydroxide ($NH_4OH$), prepared previously by diluting the commercial aqueous solution at 28%-30%, over 3 hours, while monitoring the pH by Metrohm glass pH electrode (6.0248.030), connected to the Metrohm 691 pH-meter. At the end of adding the solution, the pH of the suspension was 9.0, the whole was left under stirring in the same conditions for 64 hours, at the end of which the pH ended up at 4.3. Subsequently, to the suspension obtained, kept under stirring, was added, by peristaltic pump, a further 90 g of an aqueous solution at 15% of ammonium hydroxide ($NH_4OH$), prepared previously as described above, over 25 minutes, obtaining a suspension of pH 9.0. The suspension was left, under stirring, for 24 hours, at the end of which the pH was measured again and ended up at 8.8, and a precipitate was obtained. The precipitate obtained was filtered, washed with about 10 litres of water, and subsequently oven-dried at 120° C., for 2 hours. After drying, the solid obtained was calcined for 6 hours, at 600° C.

Synthesis of Catalyst B

To a beaker, equipped with stirring rod with Teflon crescent blade, were added 200 g of an aqueous solution at about 30% of ammonium hydroxide ($NH_4OH$), and an electrode [Metrohm glass pH electrode (6.0248.030), connected to the Metrohm 780 pH-meter] was introduced to measure the pH. In another beaker, equipped with magnetic bar stirrer, was prepared a solution of 200 g of cerium nitrate hexahydrate in 200 g of water: the cerium nitrate was then solubilised by vigorous stirring at room temperature (25° C.). The solution obtained was introduced into a dropper and fed drop by drop, over 6 minutes, into the aforementioned ammonium hydroxide solution contained in the beaker, under constant vigorous stirring. The pH of the suspension obtained was 10.1. The whole was left, under vigorous stirring, for 3 hours, during which 200 ml water was added and the pH, which was 9.6, was measured. The whole was left, under vigorous stirring, for another 1.5 hours, at the end of which another 200 ml water was added and the pH, which was 9.5, was measured again. Said suspension was left, under vigorous stirring, for 64 hours, at the end of which the pH, which was 4.5, was measured again. Subsequently, another 23 g of an aqueous solution at about 30% of ammonium hydroxide ($NH_4OH$) were added, obtaining a pH of 9.0: the whole was left, under stirring, for 6 hours, obtaining a pH of 8.5. Subsequently, 16 g of an aqueous solution at about 30% of ammonium hydroxide ($NH_4OH$) were added, obtaining a pH of 9.0. The whole was left, under vigorous stirring, for 17 hours, at the end of which the pH was 7.9, and a precipitate was obtained. The precipitate obtained was filtered, washed with 2 litres of water, and subsequently oven-dried at 120° C., for 2 hours. After drying, the solid obtained was calcined for 5 hours, at 600° C.

Dehydration Reaction

The dehydration reaction of the bio-1,3-BDO was carried out in an AISI 316L steel fixed-bed continuous tubular reactor, 400 mm long and with an internal diameter of 9.65 mm. The reactor is thermostated to the reaction temperature using an electric heater. For optimum regulation of the temperature within the reactor, along the axis thereof there is a well having external diameter 3 mm which houses the thermocouple for the temperature regulation.

The catalysts used in the tests are sieved and selected in the fraction ranging from 0.5 mm to 1 mm. The catalyst load, equal to 3 g, was inserted into the reactor between two layers of inert material (corundum), the catalytic bed was held in place by a sintered steel septum placed on the base of the reactor.

The feed-in was carried out from the top of the reactor, above the region filled with inert material, which region also acts as an evaporator and allows the reagents to pass into the gaseous state and reach the reaction temperature before coming into contact with the catalyst. The reactor thus has a down-flow setup.

The liquid reagents were fed in using a metering pump of the type used in high-performance liquid chromatography (HPLC). The gases were fed in by thermal mass flow-meter (TMF). Downstream of the reactor, the products obtained were cooled in a heat exchanger, and the condensed liquid was collected in glass vials using a series of time-controlled valves. The collected samples of liquids were analysed by gas chromatography analysis using an Agilent HP6890 gas chromatograph (GC) equipped with a Split/Splitless injector on a Quadrex 007 FFAP column of 25 m length, 0.32 diameter, 1 μm film, the carrier used was helium at a speed of 50 cm/s, the detector was a flame detector. The determination was carried out using an internal standard with calibration curves for the known individual components.

Meanwhile, the incondensable gases were analysed in an online gas chromatograph (GC) and finally sent to a volumetric drum-type gas meter, to measure the volume. The online analysis of the gases was carried out by an Agilent HP7890 gas chromatograph (GC) with HP-AI/S column of 50 m length, 0.53 mm diameter, 15 microns film, the carrier used was helium at a speed of 30 cm/s, the detector was a flame detector. The determination was carried out using an external standard with calibration curves for the known individual components.

The catalytic performances reported in Table 16 and in Table 17 are expressed by calculating the conversion of bio-1,3-BDO ($C_{1,3\text{-}BDO}$) and the butenols selectivities in accordance with the formulae below reported:

$$C_{1,3-BDO} = \frac{(\text{moles}_{1,3-BOD})_{in} - (\text{moles}_{1,3-BOD})_{out}}{(\text{moles}_{1,3-BOD})_{in}} \times 100$$

$$S_{butenols} = \frac{\text{moles}_{butenols}}{(\text{moles}_{1,3-BOD})_{in} - (\text{moles}_{1,3-BOD})_{out}}$$

wherein:
$(\text{moles}_{1,3\text{-}BDO})_{in}$=moles of 1,3-butanediol in input;
$(\text{moles}_{1,3\text{-}BDO})_{out}$=moles of 1,3-butanediol in output;
$\text{moles}_{butenols}$=total moles of alkenols [referring to 3-buten-2-ol (methylvinylcarbinol) and 2-buten-1-ol (crotyl alcohol)].

If the total of the selectivities of all the products exceeds 100%, the result of the test is expressed as selectivity for butenols normalised to 100, or:

$$S_{butenols\ normalised} = \frac{S_{butenols}}{\Sigma S_{Products}} \times 100$$

Before the catalytic test is started, the catalyst is treated in situ at 300° C., in a nitrogen flow ($N_2$). To said reactor are subsequently fed 36 g/h of an 83.3% solution of 1,3-butanediol in water at atmospheric pressure (1 bar absolute).

About 3.19 kg of Fraction 6 of "batch 05", obtained as described in Example 4 (comparative), were diluted with 640 g water. The solution obtained was fed to the dehydration reactor using catalyst A at a temperature of 370° C. without the catalyst exhibiting problems of loss of activity or loss of yield.

Subsequently, in a second test which used catalyst B, 2.135 kg of Phase III of "batch 03-2", obtained as described in Example 2 (invention) added with 428 g water were fed. The reaction temperature was set to 355° C. In this case too, the catalyst did not exhibit problems of loss of activity or loss of yield.

Table 16 reports the catalytic results obtained in terms of conversion (C %) and selectivity (S %), calculated as described above.

TABLE 16

Results of dehydration tests on purified bio-1,3-BDO obtained in Example 2 (invention) (Phase III of "batch 03-2") and Example 4 (comparative) (Fraction 6 of "batch 05")

| | Catalyst | Temperature (° C.) | Conversion (%) | Selectivity (%) | Yield (%) |
|---|---|---|---|---|---|
| Example 4 (comparative) (Fraction 6 of "batch 05") | A | 370° C. | 95 | 96 | 91 |
| Example 2 (invention) (Phase III of "batch 03-2") | B | 355° C. | 98 | 91 | 89 |

Example 8

The purified bio-1,3-BDO obtained in Example 5 (invention) (Phase III of "batch 04-2") and the purified bio-1,3-BDO obtained in Example 6 (comparative) (Fraction 4 of "batch 04-1") were subjected to catalytic dehydration, operating as follows.

For this purpose, the catalyst C was first synthesised, operating as follows.

Synthesis of Catalyst C

Preparation of a Catalyst Based on Extruded Cerium Oxide The extruded catalyst was obtained by operating as described in Example 9 of international patent application WO 2015/173780 in the name of the Applicant.

For this purpose, in a glass beaker, equipped with magnetic bar stirrer, was prepared a solution of 870 g cerium nitrate hexahydrate (99% Aldrich, product code 238538; CAS number 10294-41-4) in 4200 g of water, by vigorous stirring, at room temperature (25° C.). The solution obtained was transferred into a glass reactor, equipped with stirring rod in the form of a bar and was kept, under stirring, for 15 minutes. To the solution obtained, kept under stirring, were added, by peristaltic pump, 790 g of an aqueous solution at 15% of ammonium hydroxide ($NH_4OH$), prepared previously by diluting the commercial aqueous solution at 28%-30% (Aldrich 28%-30% $NH_3$ Basis ACS reagent; product code 221228; CAS number 1336-21-6), over 3 hours, while monitoring the pH by Metrohm glass pH electrode 6.0248.030, connected to the Metrohm 691 pH-meter. At the end of adding the solution, the pH of the suspension was 9.0:

the whole was left, under stirring, for 64 hours, at the end of which the pH ended up at 4.3. Subsequently, to the suspension obtained, kept under stirring, were added, by peristaltic pump, a further 90 g of an aqueous solution at 15% aqueous of ammonium hydroxide (NH$_4$OH), prepared previously as described above, over 25 minutes, obtaining a suspension of pH 9.0. The suspension was left, under stirring, for 24 hours, at the end of which the pH was measured again and ended up at 8.8, and a precipitate was obtained. The precipitate obtained was filtered, washed with about 10 litres of water, and subsequently oven-dried at 120° C., for 2 hours.

After said preparation had been repeated for a number of batches suitable for obtaining sufficient amounts of material, the solids obtained were combined and ground in a mortar: 1905 g of powder thus obtained were subsequently placed in an Erweka planetary mixer with AMD model motor.

The powder was dry mixed for 1 hour and, subsequently, there were added, by dropping, in sequence, 250 g of an aqueous solution at 25% of ammonium hydroxide (NH$_4$OH), prepared previously by diluting the commercial aqueous solution at 28%-30% (Aldrich 28%-30% NH$_3$ Basis ACS reagent; product code 221228; CAS number 1336-21-6), over 50 minutes, and 250 ml demineralised water, likewise over 50 minutes, obtaining a paste which was extruded using a Hutt extruder on which were mounted rollers having 2 mm holes. The pellets obtained from the extrusion were left to air-dry for two days.

Subsequently, a sample of the pellets of weight 134 g was oven-dried at 120° C., for 2 hours, and subsequently calcined for 6 hours, at 600° C., obtaining a catalyst based on cerium oxide. The catalyst is then prepared for the catalytic test by comminuting it and sieving it, selecting the fraction ranging from 0.5 mm to 1 mm.

Catalyst C, obtained as described above, was loaded into the reactor and subjected to the preliminary operations as described in Example 7. The test was started with an 83.3% 1,3-BDO solution of non-biological origin (Sigma-Aldrich B84784) in demineralised water, at a temperature of 370° C. and with a flow rate of 36 g/h.

After about 125 hours of operation, there was fed into the dehydration reactor 4.072 kg of an 83.3% solution of bio-1,3-BDO in water, obtained by suitably diluting Fraction 4 of "batch 04-1" obtained as described in Example 6 (comparative). Table 17 reports the catalytic results obtained in terms of conversion (C %) and selectivity (S %), calculated as described above. During the test, the performance remained constant, and the catalyst did not exhibit problems of loss of activity or loss of yield.

The test was continued using the 1,3-BDO starting solution of non-biological origin. In this step, the reaction temperature was set to 375° C. to recover a slight conversion loss. Subsequently, during the same test, there were fed 4.226 kg of the solution obtained by diluting with demineralised water Phase III of "batch 04-2" obtained as described in Example 5 (invention), so as to obtain an 83.3% solution. In this case too, Table 17 reports the catalytic results obtained in terms of conversion (C %) and selectivity (S %), calculated as described above. As in the previous case, the performance remained constant and the catalyst did not exhibit problems of loss of activity or loss of yield.

TABLE 17

Results of dehydration tests on purified bio-1,3-BDO obtained in Example 6 (comparative) (Fraction 4 - "batch 04-1") and Example 5 (invention) (Phase III of "batch 04-2")

| Catalyst | Temperature (° C.) | Conversion (%) | Selectivity (%) | Yield (%) |
|---|---|---|---|---|
| Example 6 (comparative) (Fraction 4 of "batch 04-1") | C | 370° C. | 94 | 96 | 90 |
| Example 5 (invention) (Phase III of "batch 04-2") | C | 375° C. | 95 | 94 | 89 |

Meanwhile, Table 18 reports the overall yield of butenols, understood as being produced between the yield of the last purification step and of the dehydration.

TABLE 18

Overall yield of butenols

| | Average yield of butenols | | | |
|---|---|---|---|---|
| | Example 2 (invention) (Phase III of "batch 03-2") [% mol] | Example 5 (invention) (Phase III of "batch 04-2") [% mol] | Example 4 (comparative) (Fraction 6 of "batch 05") [% mol] | Example 6 (comparative) (Fraction 4 of "batch 04-1") [% mol] |
| Distillation (comparative) | — | — | 84 | 88 |
| Evaporation (three steps) (invention) | 97 | 96 | — | — |
| Dehydration to butenols | 89 | 89 | 91 | 90 |
| Average overall yield | 86 | 85 | 76 | 79 |

From the data reported in Table 18, it may be seen that the process according to the present invention for producing bio-butenols from a fermentation broth is an improvement on the prior art in terms of average overall yield.

The invention claimed is:

1. A process for bio-1,3-butanediol purification from a fermentation broth, the process comprising the following steps:
    (a) subjecting the fermentation broth to separation;
    (b) subjecting the product obtained in step (a) to treatment with ion-exchange resins;
    (c) subjecting the product obtained in step (b) to a first evaporation at a temperature ranging from 30° C. to 100° C. and/or at a pressure ranging from 5 mbar to 100 mbar;
    (d) subjecting the product obtained in step (c) to a second evaporation; and
    (e) subjecting the product obtained in step (d) to a third evaporation, thereby obtaining purified bio-1,3-butanediol.

2. The process according to claim 1, wherein step (a) comprises the following steps:
    ($a_{1a}$) microfiltration; and
    ($a_2$) nanofiltration.

3. The process according to claim 1, wherein step (a) comprises the following steps:
- ($a_{1b}$) centrifugation; and
- ($a_2$) nanofiltration.

4. The process according to claim 2, wherein step ($a_{1a}$) is carried out:
- by membranes having a mean pore diameter ranging from 0.01 μm to 1.0 μm; and/or
- operating at a transmembrane pressure ranging from 0.1 bar to 8 bar, the transmembrane pressure being defined as an average pressure between a pressure measured upstream and a pressure measured downstream of a microfiltration module; and/or
- at a temperature ranging from 20° C. to 90° C.; and/or
- by ceramic membranes that are submerged or in a cross flow configuration or in a dynamic cross flow configuration, or by flat or hollow-fibre polymer membranes that are submerged or in a cross flow configuration.

5. The process according to claim 3, wherein step ($a_{1b}$) is carried out:
- at a temperature ranging from 20° C. to 90° C.; and/or
- operating at a centrifugal feed rate ranging from 50 l/h to 1000 l/h; and/or
- at a rotation speed ranging from 2000 rpm to 50000 rpm.

6. The process according to claim 2, wherein step ($a_2$) is carried out:
- by nanofiltration membranes having a molecular weight cut-off (MWCO) ranging from 100 daltons to 500 daltons; and/or
- by nanofiltration membranes having a maximum operating temperature ranging from 15° C. to 100° C.; and/or
- operating at a transmembrane pressure ranging from 10 bar to 50 bar, the transmembrane pressure being defined as an average pressure between a pressure measured upstream and a pressure measured downstream of a nanofiltration module.

7. The process according to claim 1, wherein step (b) comprises the steps:
- ($b_1$) an anion exchange step; and
- ($b_2$) a cation exchange step.

8. The process according to claim 7, wherein step ($b_1$) is carried out with a column containing a weak anionic resin.

9. The process according to claim 7, wherein step ($b_2$) is carried out with a column containing a strong cationic resin.

10. The process according to claim 7, wherein steps ($b_1$) and ($b_2$) are carried out at a flow rate in litres of product obtained in step (a) per hour ranging from 2 BV/h to 4 BV/h, wherein BV is Bed Volume which is volume of resin per single column.

11. The process according to claim 7, wherein the product obtained from steps ($b_1$) and ($b_2$) has a residual conductivity ranging from 0.1 μS/cm to 100 μS/cm.

12. The process according to claim 7, wherein the product obtained in step (a) is fed to step ($b_1$) and subsequently to step ($b_2$), or is fed to step ($b_2$) and subsequently to step ($b_1$).

13. The process according to claim 1, wherein step (d) is carried out:
- at a temperature ranging from 30° C. to 150° C.; and/or
- at a pressure ranging from 1 mbar to 100 mbar.

14. The process according to claim 1, wherein (e) is carried out:
- at a temperature ranging from 30° C. to 150° C.; and/or
- at a pressure ranging from 5 mbar to 100 mbar.

15. A process for bio-1,3-butanediol purification from a fermentation broth, the process comprising the following steps:
- (a) subjecting the fermentation broth to separation;
- (b) subjecting the product obtained in step (a) to treatment with ion-exchange resins;
- (c) subjecting the product obtained in step (b) to a first evaporation;
- (d) subjecting the product obtained in step (c) to a second evaporation; and
- (e) subjecting the product obtained in step (d) to a third evaporation, thereby obtaining purified bio-1,3-butanediol, wherein step (b) includes an anion exchange step ($b_1$) and a cation exchange step ($b_2$), wherein steps ($b_1$) and ($b_2$) are carried out at a flow rate in litres of product obtained in step (a) per hour ranging from 2 BV/h to 4 BV/h, and wherein BV is Bed Volume, which is volume of resin per single column.

16. A process for bio-1,3-butanediol purification from a fermentation broth, the process comprising the following steps:
- (a) subjecting the fermentation broth to separation;
- (b) subjecting the product obtained in step (a) to treatment with ion-exchange resins;
- (c) subjecting the product obtained in step (b) to a first evaporation;
- (d) subjecting the product obtained in step (c) to a second evaporation at a temperature ranging from 30° C. to 150° C. and/or at a pressure ranging from 1 mbar to 100 mbar; and
- (e) subjecting the product obtained in step (d) to a third evaporation, thereby obtaining purified bio-1,3-butanediol.

17. A process for bio-1,3-butanediol purification from a fermentation broth, the process comprising the following steps:
- (a) subjecting the fermentation broth to separation;
- (b) subjecting the product obtained in step (a) to treatment with ion-exchange resins;
- (c) subjecting the product obtained in step (b) to a first evaporation;
- (d) subjecting the product obtained in step (c) to a second evaporation; and
- (e) subjecting the product obtained in step (d) to a third evaporation at a temperature ranging from 30° C. to 150° C. and/or at a pressure ranging from 5 mbar to 100 mbar, thereby obtaining purified bio-1,3-butanediol.

* * * * *